United States Patent [19]

Mjalli et al.

[11] Patent Number: 5,723,451
[45] Date of Patent: Mar. 3, 1998

[54] NITRIC OXIDE SYNTHASE (NOS) INHIBITORS

[75] Inventors: Adnan M. M. Mjalli, Vista; Sepehar Sarshar, Cardiff; Chengzhi Zhang, Carlsbad, all of Calif.

[73] Assignee: Ontogen Corporation, Carlsbad, Calif.

[21] Appl. No.: 694,998

[22] Filed: Aug. 9, 1996

[51] Int. Cl.$^6$ .................................................. A61K 31/495
[52] U.S. Cl. .................................................. 514/255
[58] Field of Search ................................. 514/255

[56] References Cited

U.S. PATENT DOCUMENTS 4,882,339  11/1989  Wasley ............................. 514/319

*Primary Examiner*—Theodore J. Criares
*Attorney, Agent, or Firm*—Frank S. Chow

[57] ABSTRACT

There are disclosed methods useful for the inhibition of inducible nitric oxide synthase by the adminstration of a compound of the Formula I:

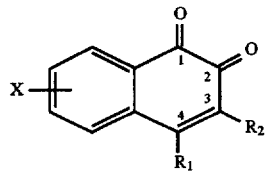

to a patient in need of such inhibition such as hypotension, inflammation, autoimmune diseases and septic shock and the like.

11 Claims, No Drawings

NITRIC OXIDE SYNTHASE (NOS) INHIBITORS

BACKGROUND OF THE INVENTION

1. Field of the Invention

The present invention relates to the use of compounds which are inhibitors of nitric oxide synthase (NOS). The present invention also includes within its scope methods of treatment where nitric oxide is involved in the biological functions of the human body, e.g. hypotension, inflammation, the damage due to inflammation, acute and/or chronic pain, neuronal disorders such as stroke, memory disorders, and depression, autoimmune diseases, including allograft rejection, diabetes, septic and endotoxic shock and the like.

2. Background of the Art

Nitric oxide is an important component of endothelium-derived relaxing factors (EDRFs). EDRFs have been shown to be involve in the regulation of blood flow and vascular resistance. In addition to the vascular endothelium, macrophages have also been reported to produce nitric oxide in the body which is a component of their cell killing and/or cytostatic function. Nitric oxide is produced in mammalian cells by nitric oxide synthase (NOS) by conversion of L-arginine to citrulline. Moncada, S., Palmer, R. M. J., and Higgs, E. A. (1991) Pharm. Rev. 43, 109–142.; Nathan, C. (1992) FASEB J. 6, 3051–3064; Jacob, T. D., Morrell, M. K., Manzi, S., Ochoa, J. B., Verdile, V., Udekwu, A. O., Berceli, S. A., Simmons, R. L., and Peitzman, A. B. (1992) in Nitric Oxide: Implications for Drug Research, P. 28, IBC, South Natick, Mass.; Langrehr, J. M., Murase, N., Markus, P. M., Cai, X., Nenhaus, P., Schraut, W., Simmons, R. L., and Hoffman, R. A. (1992) J. Clin. Invest. 90, 679–683; Corbett, J. A., Tilton, R. G., Chang, K., Hasan, K. S., Ido, Y., Wang, J. L., Sweetland, M. A., Lancaster, J. R. Jr., Williamson, J. R., and McDaniel, M. L. (1992) Diabetes 41, 552–556; Griess, P. (1879) Chem. Ber. 12 426.

There are three distinct isoforms of human NOS, neuronal (bNOS), endothelial (eNOS) and inducible (iNOS).

In general eNOS is constitutively expressed and produces reletively low levels of NO. Activity of eNOS is dependent on $Ca^{2+}$ influx. eNOS is found in vascular smooth muscle cells which is not identical to the form of enzyme found in neurons. Formation of NO by the eNOS in vascular endothelial cells is believed to play a role in regulating blood pressure by relaxing muscles and allowing the vessel to dialate, which lower the blood pressure Pollock, J. S., Forstermann, U., Mitchell, J. A., Warner, T. D., Schmidt, H. H. H. W., Nakane, M. and Murad, F. (1991) Proc. Natl. Acad. Sci. USA 88, 10480–10484; Lamas, S., Marsden, P. A., Li, G. K., Tempst, P. and Michel, T. (1992) Proc. Natl. Acad. Sci. USA 89, 7773–7777.

Disruption of the neuronal NOS (second isoform of NOS) gene causes no histological abnormalities in the central nervous system Huang, P. L., Dawson, T. M., Bredt, D. S., Snyder, S. H. and Fishman, M. C. (1993) Cell 75, 1273–1286.

iNOS is not dependent on elevated $Ca^{2+}$ concentration and generally expressed only after induction by certain cytokines or by bacterial lipopolysaccharide (LPS) Wei, X. Q., Charles, I. G., Smith, A., Ure, J., Feng, G. J., Huang, F. P., Xu, D., Muller, W., Moncada, S. and Liew, F. Y. (1995) Nature (London) 375, 408–411.

It is thought that in sepsis or cytokine-induced shock, excess production of nitric oxide by iNOS plays an important role in life-threatening hypotension. Evidence for this has come from observations that serum levels of NO oxidation products are elevated in animals and humans undergoing septic shock and from in vivo studies with NOS inhibitors Goode, H. F., Howdle, P. D., Walker, B. E. and Webster, N. R. (1995) Clin. Sci. 88, 131–133; Barthlen, W., Stadler, J., Lehn, N. L., Miethke, T., Bartles, H. and Siewert, J. R., (1994) Shock 2, 398–401; Cunha, F. Q., Assreuy, J., Mass, D. W., Rees, D., Leal L. M. C., Moncada, S. and Carrier, M. (1994) Immu. 81, 211–215.

Furthermore, it has been postulated that excess production of nitric oxide by iNOS is a factor in the unresponsiveness to pressor agents such as $alpha_1$-adrenergic agonists employed in the treatment of septic or cytokine-induced shock patients.

We are now describing a new class of compounds useful as inhibitors of iNOS. See for example the paper presented by Mosby et al. reported in J. Org. Chem., 24, 374–380 (1959) entitiled "Reactions of 2,3-dichloro-1,4-naphthoquinone with 2, Aminopyridine and Related Amines", Offenlegungsschrift DE 3926747 A1 entitled "1,2-Naphthochinone enthalende fungizide Mittel", Asahi et al., Chem. Pharm. Bull., 32, 3093–3099 (1984), and Carroll et al. J. Heterocycl. Chem. 7, 297–306 (1970). These compounds are described below.

SUMMARY OF THE INVENTION

The present invention relates to the use of compounds of general formula 1 which are inhibitors of NOS:

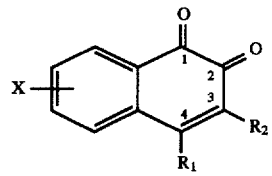

FORMULA 1 wherein when $R_2$ is H; $R_1$ is selected from the group consisting of:

1) —NH—$C_0$–$C_{10}$ alkyl -aryl, N—($C_0$–$C_{10}$ alkyl substituted aryl)$_2$, —($C_0$–$C_{10}$alkyl substituted aryl, —N($C_0$–$C_{10}$alkyl substituted aryl)$_2$ ($C_0$–$C_{10}$ alkyl), in which "aryl" is optionally attached to compound 1 through C or N and is selected from the group consisting of isoindanolyl, isoindolinyl, tetrahydroquinolyl, phenyl, naphthyl, pyridyl, furyl, pyrryl, thienyl, isothiazolyl, imidazolyl, benzimidazolyl, triazolyl, tetrazolyl, pyrazinyl, pyrimidyl, quinolyl, isoquinolyl, benzofuryl, benzothienyl, pyrazolyl, indolyl, isoindolyl, purinyl, carbazolyl, isoxazolyl, thiazolyl, oxazolyl, benzthiazolyl, and benzoxazolyl; and the term "substituted aryl" denotes mono-, di- and/or tri-substituted aryl wherein aryl is as defined above and in which the substituents are independently selected from the group consisting of H, trifluoromethyl, amino, hydroxy, halo, nitro, —O—$C_1$–$C_6$ alkyl, —S—$C_1$–$C_6$ alkyl, —NH—$C_1$–$C_6$ alkyl, —N($C_1$–$C_6$ alkyl)$_2$, —C(O) —$C_1$–$C_6$ alkyl, C(O) NH$C_0$–$C_{10}$alkyl, —NHC(O) $C_1$–$C_6$ alkyl, —$C_1$–$C_{11}$ $CO_2R$ or $C_1$–$C_6$NHR, —$C_1$–$C_{11}$ CONHR, carboxy, —C(O)O $C_1$–$C_6$ alkyl; trans-CH=CH$CO_2R$; trans CH=CHCONHR wherein R=$C_1$–$C_{11}$ alkyl or $C_1$–$C_{11}$ alkylphenyl;

2) Cyclic —$N(CH_2CH_2)_2$ Y, cyclic $NCHA(CH_2)_{3-4}$, or —NH $C_2$–$C_{11}$ alkyl-W wherein:

A= i) $C_1$-$C_{10}$ alkyl, $C_1$-$C_{10}$alkylaryl or, ii) $COZR_3$ wherein Z=oxygen, NH and $R_3$=H, or $C_1$-$C_{10}$ alkyl, or $C_0$-$C_{10}$ alkylaryl wherein aryl group is as defined in (1) above, and Y= i) oxygen, or S, or NH or ii) $NC_0$-$C_{10}$alkyl or iii) N $C_1$-$C_{10}$alkylsubstituted aryl, iv) NC=$ZMR_3$ wherein Z=oxygen, or NH; M=C, oxygen, N, and $R_3$ is $C_0$-$C_{10}$alkyl substituted aryl wherein "substituted aryl" is as defined above;

v) $N(C_1$-$C_{10})CH(COZR_3)(NHCOZR_3)$ wherein Z and $R_3$ are as defined above;

and W= i) $NH_2$ ii) $NHC_0$-$C_{10}$alkylaryl where aryl is as defined in 1 or iii) $ZC(O)MR_3$ wherein Z, M and $R_3$ is as defined above;

$R_2$ is hydrogen; or $R_1$ and $R_2$ taken together forming another aryl group; and X is hydrogen, halo, alkyl, alkoxy, hydroxy, nitro, amino, trifluoromethyl and aryl.

Briefly, the compounds described herein are indicated in the prophylaxis or treatment for a patient suffering from hypotension caused by an excess production of nitric oxide from arginine in vascular cells in the patient induced by therapy with a cytokine, or exposure to a bacterial endotoxin, i.e. septic shock or from immunosuppressant therapy.

The present invention also includes within its scope methods of adminstrating to said patient a therapeutically effective amount, i.e. an effective NOS inhibitory mount of a compound or the corresponding pharmaceutically acceptable salt, ester or solvate selected from the compounds depicted in Formula 1 in an inert pharmaceutical carrier.

Among the preferred compounds for iNOS inhibition are those compounds wherein $R_1$ is aniline or substituted aniline, and the following:

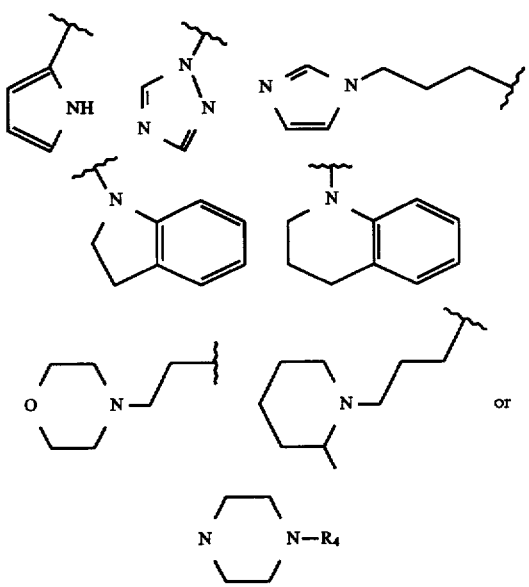

in which $R_4$ is alkyl as defined above or:

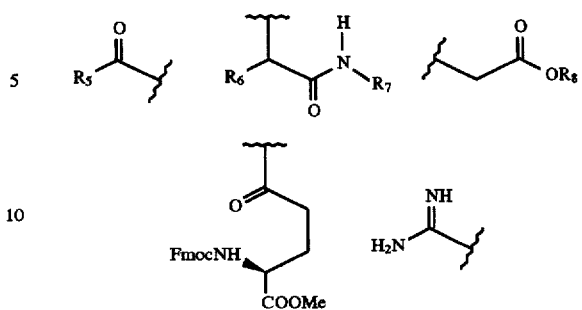

in which $R_5$, $R_6$, $R_7$ and $R_8$ are alkyl, aryl or substituted aryl as defined above.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of Formula 1, where a basic or acidic group is present in the structure, are also included within the scope of this invention. When an acidic substituent is present, such as —COOH, there can be formed the ammonium, sodium, potassium, calcium salt, and the like, which can be formulated into dosage forms suitable for oral or parenteral adminstration. When a basic group is present, such as amino or a basic heteroaryl radical, such as pyridyl, an acidic salt, such as hydrochloride, hydrobromide, acetate, maleate, pamoate, methanesulfonate, p-toluenesulfonate, and the like, can be formulated into suitable dosage form for oral or parenteral adminstration form.

Also, in the case of the —COOH being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds useful in this invention may form solvates with water or common organic solvents. Such solvates are useful in the methods of treatment of this invention.

The term "therapeutically effective amount" or "effective NOS inhibitory amount" shall mean that amount of compound, as depicted in Formula 1 or its pharmaceutical salt, ester etc. that will elicit the biological or NOS inhibitory response of a tissue, system, animal, or human that is being sought by a researcher, veterinarian, medical doctor or other clinician.

According to the present invention, compounds of Formula 1 are prepared according to the following general reaction Scheme A and/or Scheme B:

Scheme A

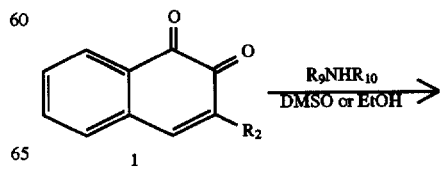

1

-continued
Scheme A

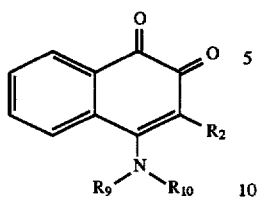

Scheme B

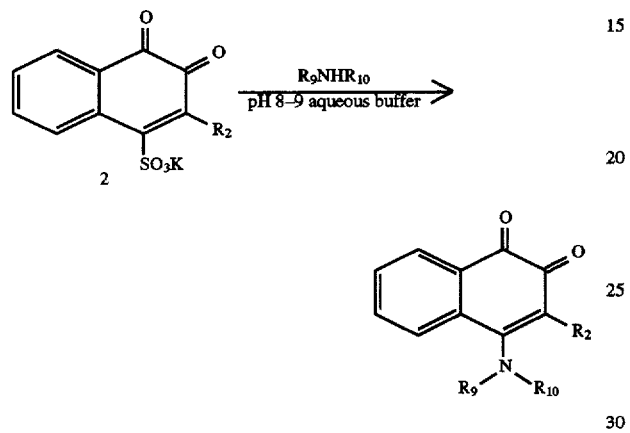

The commercially available 1,2-naphthoquinones 1 or 2 is reacted with the appropriate amine at equal molar ratio in a proper reaction solvent such as DMSO or a lower molecular weight alcohol, such as ethanol (Scheme A, at about 60° C.) or in a pH 8–9 aqueous buffer solution (Scheme B, at room temperature) as described above. The reaction products are recovered from the reaction mixtures by the partition between an organic solvent such as ethyl acetate, methylene chloride, and chloroform and water. The organic layer is then dried with sodium sulfate and evaporated in vacuo, yielding the desired products as the residue.

In accordance with the procedure described in Scheme A, the following compounds were prepared:

Example 1

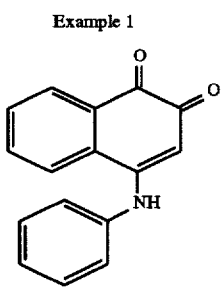

Example 2

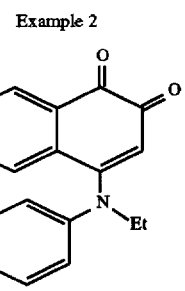

Example 3     Example 4

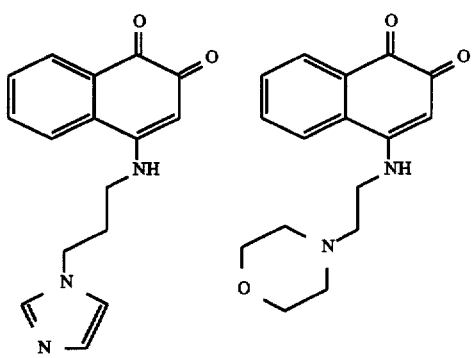

Example 5     Example 6

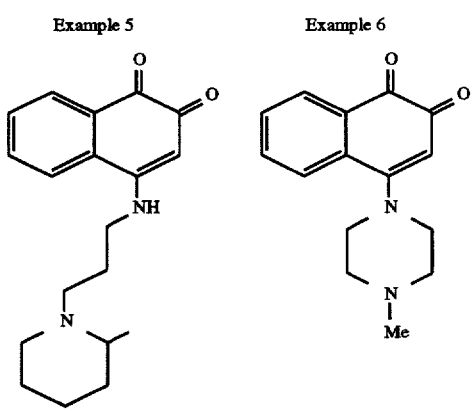

Example 7

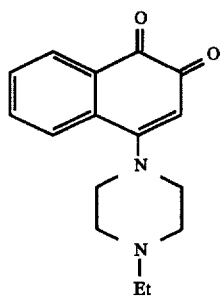

Example 8

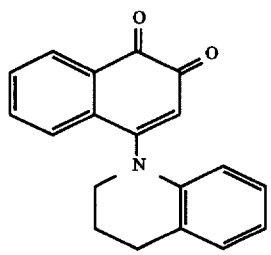

Example 9     Example 10

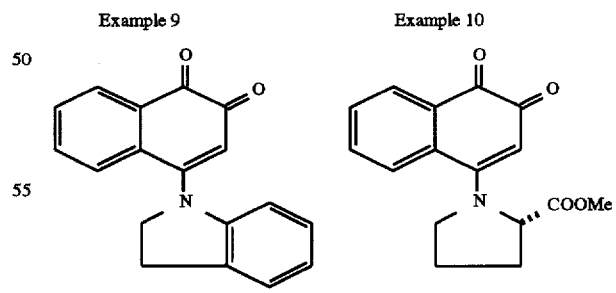

Example 11

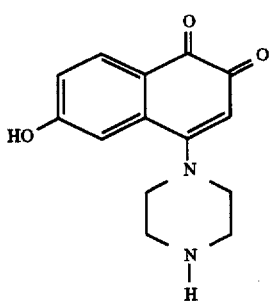

In accordance with the procedure described in Scheme B, the following compounds were prepared:

Example 12

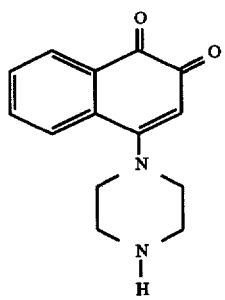

Example 13

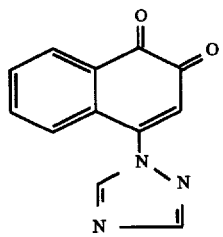

Example 14

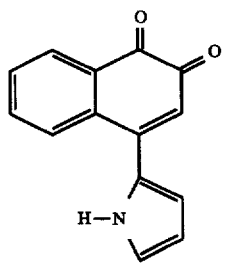

Example 15

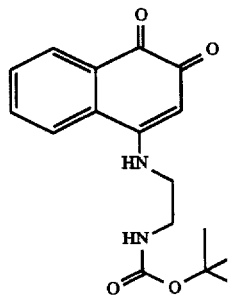

Example 16

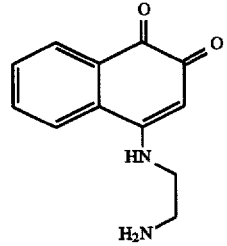

The following compounds were prepared by treatment of compound of 12 using standard acylation reaction such as with an acid chloride, a carboxylic acid, carbonyl diimidazole, isocyanate, and 1H-pyrazole-1-carboxamidine hydrochloric acid.

Example 17

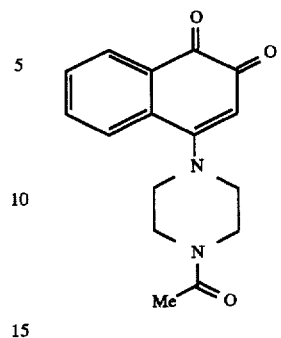

Example 18

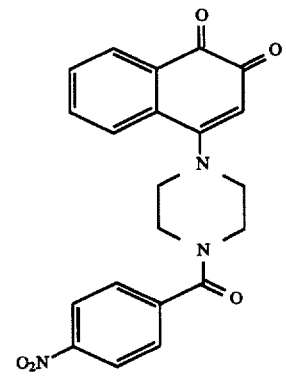

Example 19

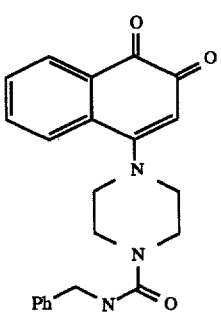

Example 20

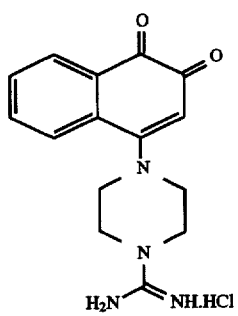

Example 21

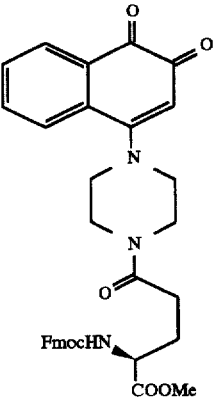

Example 22

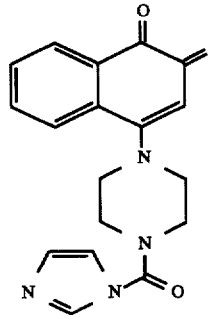

Compound 22 was prepared from the reaction of compound 12 t-butyl a-bromoacetate under standare conditions.

Example 23

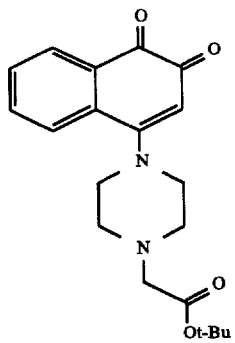

Compound 23 was prepared in accordance with the procedure described by Mosby et al. reported in *J. Org. Chem.*, 24, 374–380 (1959).

Example 24

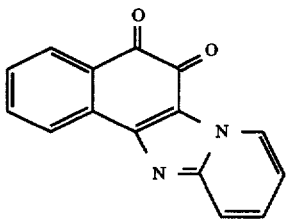

The Compounds depicted in Formula 1 which are useful as NOS inhibitors were tested in accordance with the procedure described by Stuehr, et al. "Purification and characterization of the cytokine-induced macrophage nitric oxide synthase: an FAD- and FMN-containing flavoprotein." *Proc. Natl. Acad. Sci. USA*, 88, 7773-7 (1991). Thus, iNOS was isolated from interferon-g and lipopolysaacharide (LPS) stimulated mouse macrophage cells (RAW 264.7 cells). RAW cells were incubated overnight with interferon-G and LPS. A lysate fraction was prepared by lysing the harvested cells in liquid nitrogen and thawing by incubation in a 37° C. water bath and run over an ADP sepharose column for partial purification. The assay was validated and optimized.

bNOS was isolated according to the proceedure disclosed in Proc. Nat. Acad. Sci. USA Vol. 88 pp. 365–369, January 1991. To a 96-well microtiter plate the following were added:

35 mL assay buffer (with/$^3$H Arg.)
10 mL bNOS crude extract and
5 mL inhibitor at 10 X FAC The resulting solution was incubated at 37° C. for 20 minutes. The reaction was stopped by the addition of 75 ml of a Stop buffer.

Then 125 ml of 1:1 DOWEX AG50 WX-8 was added with gentle mixing. After 15 minutes, 50 mL of the supernatent was counted with 200 mL of a scintillation fluid in a Packard microscintillater.

The solutions had the following composition:

| Assay Buffer: | |
|---|---|
| 50 mM | Tris pH7.8 |
| 200 mM | NADPH |
| 10 mM | BH$_4$ |
| 10 mM | FAD |
| 10 mM | FMN |
| 4 mM | CaCl$_2$ |
| 20 mg/mL | calmodulin |
| 4 mM | L-Arg |
| .35 mCi/well | $^3$H-L-Arg |
| Stop Buffer: | |
| 100 mM | Hepes pH 5.5 |
| 1 mM | L-Citrulline |
| 10 mM | EGTA |

Nitric Oxide Synthase activity was assayed by adding 10 mL of crude lysate 10 mL of substrate and 10 mL of a selected Compound as depicted in Formula 1 in DMSO to 70 mL of assay buffer in a 96-well microtiter plate. The wells were mixed gently and incubated for 90 minutes at 37° C. The reaction was stopped by adding 2 units of L-lactic dehydrogenase (5 mL of stock solution) and 5 mmole of sodium pyruvate (10 mL of stock solution). The solution was incubated for an additional 15 minutes at 37° C. 100 mL of Griess reagent was added and read absorbance at 560 nm. The inhibitory concentraction 50 or IC$_{50}$ for the Compounds depicted in examples 1–24 as follows:

| | IC$_{50}$ (mM) or Percentage Inhibition | |
|---|---|---|
| Examples | iNOS | bNOS |
| 1 | 27 | —* |
| 2 | 16 | — |
| 3 | 41 | — |
| 4 | 45 | — |
| 5 | 12 | — |
| 6 | 5.4 | 2.0 |
| 7 | 8 | — |
| 8 | 13 | — |
| 9 | 17 | — |
| 10 | 44 | — |
| 11 | 34% @ 10 mM | — |
| 12 | 9.9 | 2.1 |
| 13 | 7.8 | — |
| 14 | 7.4 | — |
| 15 | 3.8 | 1.1 |
| 16 | 11.2 | 3.2 |
| 17 | 5.4 | — |
| 18 | 6.2 | 1.2 |
| 19 | 2.2 | 2.1 |
| 20 | 0.67 | 0.57 |
| 21 | 15.6 | 1.9 |
| 22 | 7.3 | 3.9 |
| 23 | 93% @ mM | — |
| 24 | 2.3 | 0.27 |

Footnote:
*'—' means the data is not available.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

A compound of Formula 1 may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula 1 are employed.

Generally speaking, the selected compound is administered at a dosage level of from about 0.1 mg to about 200 mg/kg of the body weight of the subject being treated. This dosage has to be individualized by the clinician based on the specific clinical condition of the subject being treated.

To enhance the therapeutic spectrum of the methods of the present invention, the selected NOS inhibitors may be combined with or replace other therapeutic agents such as alpha$_1$-adrenergic modulators which are currently being used to treat hypotension in septic or cytokine treated patients. These modulators include, for example, epinephrine, norepinephrine dopamine and the like. Again, the dosage needs to be individualized by the clinician.

We claim:

1. A method for the inhibition of nitric oxide synthase in a subject in need of such inhibition which comprises the administration of an effective amount of nitric oxide synthase inhibitor wherein the inhibitor has the formula:

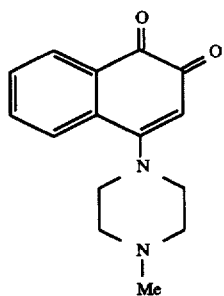

2. A method according to claim 1 wherein the compound has the formula:

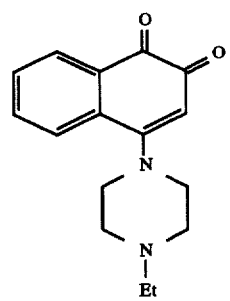

3. A method according to claim 1 wherein the compound has the formula:

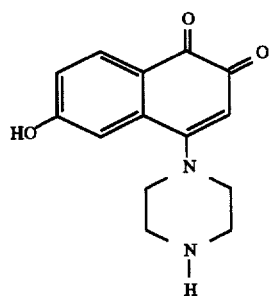

4. A method according to claim 1 wherein the compound has the formula:

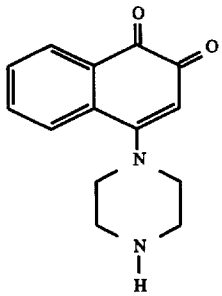

5. A method according to claim 1 wherein the compound has the formula:

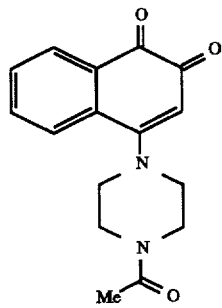

6. A method according to claim 1 wherein the compound has the formula:

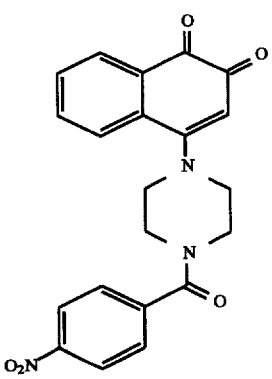

7. A method according to claim 1 wherein the compound has the formula:

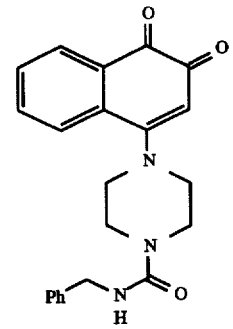

8. A method according to claim 1 wherein the compound has the formula:

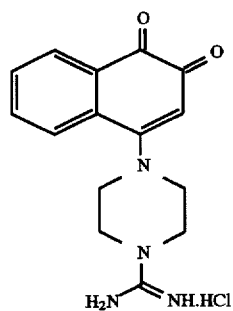
9. A method according to claim 1 wherein the compound has the formula:
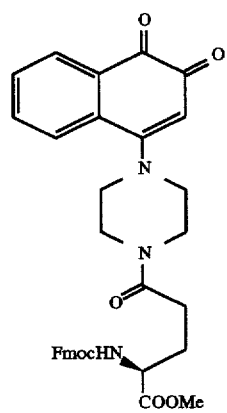
10. A method according to claim 1 wherein the compound has the formula:
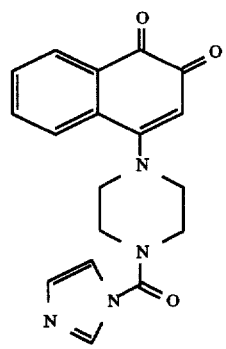
11. A method according to claim 1 wherein the compound has the formula:
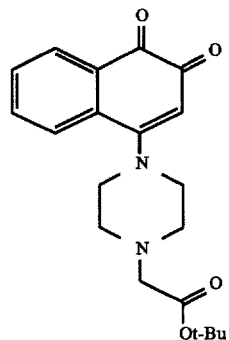
* * * * *

UNITED STATES PATENT AND TRADEMARK OFFICE
CERTIFICATE OF CORRECTION

PATENT NO : 5,723,451
DATED : Mar. 3, 1998
INVENTOR(S): Adnan M.M. Mjalli, Sephar Sarshar, Chengzhi Zhang It is certified that error appears in the above-identified patent and that said Letters Patent is hereby corrected as shown below:

Please add the following claim:

Claim 1 – A method for the inhibition of nitric oxide synthase (NOS) in a subject in need of such inhibition which comprises the administration of an effective amount of nitric oxide synthase (NOS) inhibitors of a compound of Formula I

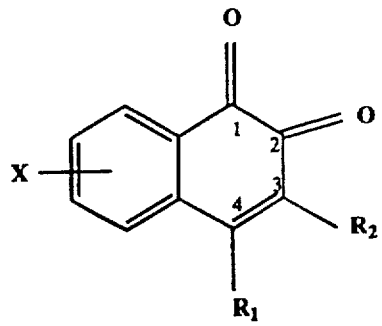

Formula I wherein $R_2$ is H and $R_1$ is selected from the group consisting of

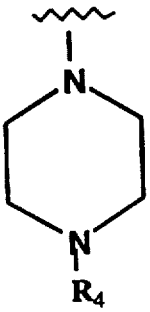

UNITED STATES PATENT AND TRADEMARK OFFICE
CERTIFICATE OF CORRECTION

PATENT NO : 5,723,451
DATED : Mar. 3, 1998
INVENTOR(S): Mjalli, Sarshar, Zhang

It is certified that error appears in the above-identified patent and that said Letters Patent is hereby corrected as shown below:

in which $R_4$ is hydrogen, alkyl or

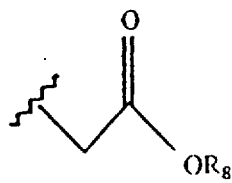
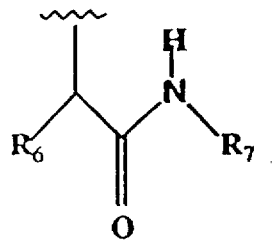
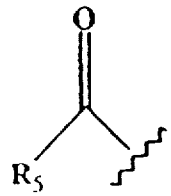

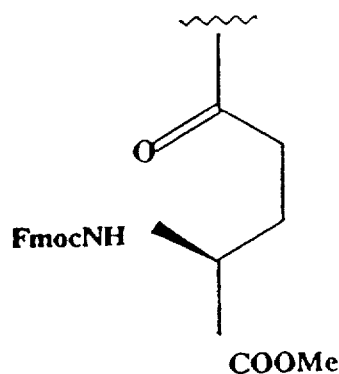

Or

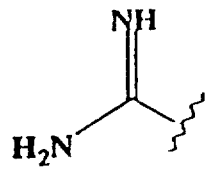

In the above, $R_5$, $R_6$, $R_7$ and $R_8$ are alkyl, aryl or substituted aryl. Please renumber claims "1" to read "2", "2" to read "3", "3" to read "4", "4" to read "5", "5" to read "6", "6" to read "7", "7" to read "8", "8"

UNITED STATES PATENT AND TRADEMARK OFFICE
CERTIFICATE OF CORRECTION

PATENT NO. : 5,723,451
DATED : Mar. 3, 1998
INVENTOR(S) : Mjalli, Sarshar, Zhang It is certified that error appears in the above-identified patent and that said Letters Patent is hereby corrected as shown below:

to read "9", "9" to read "10", "10" to read "11", and "11" to read "12".

Signed and Sealed this

Twelfth Day of May, 1998

Attest:

Attesting Officer

BRUCE LEHMAN

Commissioner of Patents and Trademarks